(12) United States Patent
Stein et al.

(10) Patent No.: US 6,867,043 B2
(45) Date of Patent: Mar. 15, 2005

(54) PEPTIDES THAT DELIVER ANTISENSE OLIGONUCLEOTIDES WHICH DOWNREGULATE PROTEIN EXPRESSION IN CELLS

(75) Inventors: Cy A. Stein, New City, NY (US); Luba Benimetskaya, New York, NY (US); Nancy Guzzo-Pernell, Melbourne (AU)

(73) Assignee: The Trustees of Columbia University in the City of New York, New York, NY (US)

( * ) Notice: Subject to any disclaimer, the term of this patent is extended or adjusted under 35 U.S.C. 154(b) by 262 days.

(21) Appl. No.: 10/002,884

(22) Filed: Nov. 2, 2001

(65) Prior Publication Data

US 2003/0087810 A1 May 8, 2003

(51) Int. Cl.$^7$ ................................................ C12N 15/63
(52) U.S. Cl. ........................... 435/455; 435/6; 435/325; 435/375; 536/23.1; 536/24.5; 530/326; 530/322
(58) Field of Search .......................... 514/44; 536/23.1, 536/24.5; 435/6, 325, 375

(56) References Cited

U.S. PATENT DOCUMENTS 5,959,096 A 9/1999 Bennett

OTHER PUBLICATIONS

Tamm, I. et al. The Lancet. 2001, Aug. 358: 489–497.*
Agrawal et al., TIBTECH 1996. 14:376–380□□.*
Gewirtz et al., 1996. Proc. Natl. Acad. Sci. v 93, pp. 3161–3163□□.*
Braasch, D. A. Biochemistry. Apr. 2002; 41(14): 4503–4510□□.*
Branch, A. D., (1998).Trends Biochem Sci. Feb.; 1998 23(2):45–50□□.*
Oehlke et al. Cellular Uptake of Antisense Oligonucleotides After Complexing or Conjugation with Cell–penetrating Model Peptides, *Eur. J. of Mol. Biol.* (2002) 269 (16) :4025–32; and.
Okuda et al. Antisense Delivery into Mitochondria Using Peptide, *Proceedings—28$^{th}$ International Symposium on Controlled Release of Bioactive Materials and 4$^{th}$ Consumer and Diversified products Conference* (2001) 2:1237–1238.
De La Torre, B., Albericio, F., Saison–Behmoaras, E., Bachi, A., and Eritja, R. (1999) *Bioconjugate Chem.*, 10:1005–1–12 (Exhibit 3).
Eritja, R., Pons, A., Escarceller, M., Giralt, E., and Albericio, R. (1991) *Tetrahedron* 47:4113–4120 (Exhibit 4).
Neves, C., Byk, G., Scherman, D., and Wils, P. (1999) *FEBS Lett.* 453:41–45 (Exhibit 5).
Morris, M.C., Vidal, P. Chaloin, L., Heitz, F., and Divita, G. (1997) *Nucl. Acids Res.* 25:2730–2736 (Exhibit 6) and.
Pichon C, Roufai MB, Monsigny M, Midoux P. (2000) Histidylated oligolysines increase the transmembrane passage and the biological activity of antisense oligonucleotides. *Nucl. Acids Res.* 28: 504–512 (Exhibit 8).

* cited by examiner

Primary Examiner—John L. LeGuyader
Assistant Examiner—J D Schultz
(74) Attorney, Agent, or Firm—John P. White; Cooper & Dunham LLP

(57) ABSTRACT

The present invention provides a peptide that can complex with an oligonucleotide, e.g. an antisense oligonucleotide, and deliver it into a cell. The present invention also provides compositions comprising a complex of such a peptide and an oligonucleotide and methods of delivering an oligonucleotide into a cell and of inhibiting protein expression using such compositions. The present invention also provides a method of making such a complex, a method of sensitizing cells to anti-cancer agents such as paclitaxel, and pharmaceutical compositions.

26 Claims, 9 Drawing Sheets

| R-Long peptide-NLS, μM | 25 | 18.8 | 12.5 | 3.13 | - |
|---|---|---|---|---|---|
| ISIS 3521, μM | 2 | 1.5 | 1 | 0.25 | - |
| Chloroquine (25 μM) | | | | | |

\* control untreated cells

*PC3 cells*

*Figure 5*

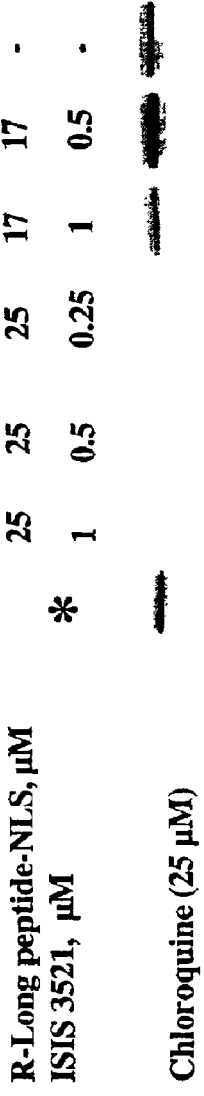
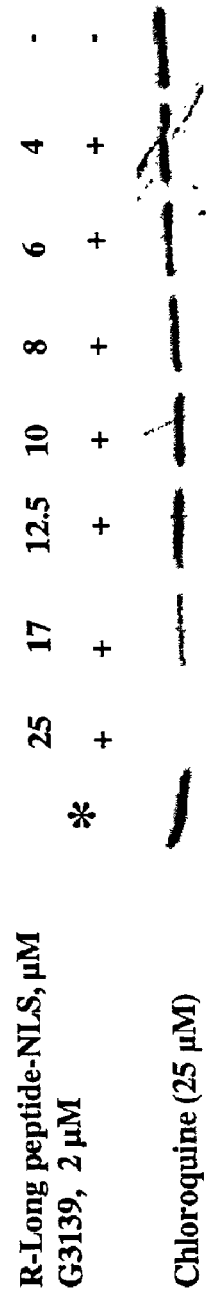
Figure 7A
Figure 7B
PC3 cells
* control untreated cells

* control untreated cells

PC3 cells

SEQUENCE LISTING

<160> NUMBER OF SEQ ID NOS: 9

<210> SEQ ID NO 1
<211> LENGTH: 32
<212> TYPE: PRT
<213> ORGANISM: ARTIFICIAL SEQUENCE
<220> FEATURE:
<223> OTHER INFORMATION: NOVEL PEPTIDE - SV40/PROTAMINE SOURCE

```
<400> SEQUENCE: 1

Arg Arg Arg Arg Ser Arg Arg Arg Arg Arg Phe Gly Arg Arg
1               5                   10                  15

Arg Arg Arg Val Trp Arg Arg Arg Pro Lys Lys Lys Arg Lys Val
                20                  25                  30

<210> SEQ ID NO 2
<211> LENGTH: 21
<212> TYPE: PRT
<213> ORGANISM: ARTIFICIAL SEQUENCE
<220> FEATURE:
<223> OTHER INFORMATION: NOVEL PEPTIDE - SV40/PROTAMINE SOURCE

<400> SEQUENCE: 2

Arg Arg Arg Arg Arg Arg Trp Gly Arg Arg Arg Arg Arg Pro Lys
1               5                   10                  15

Lys Lys Arg Lys Val
                20

<210> SEQ ID NO 3
<211> LENGTH: 21
<212> TYPE: PRT
<213> ORGANISM: ARTIFICIAL SEQUENCE
<220> FEATURE:
<223> OTHER INFORMATION: CONTROL PEPTIDE

<400> SEQUENCE: 3

Arg Arg Arg Arg Arg Arg Trp Gly Arg Arg Arg Arg Arg Pro Lys
1               5                   10                  15

Gly Lys Arg Lys Val
                20

<210> SEQ ID NO 4
<211> LENGTH: 31
<212> TYPE: PRT
<213> ORGANISM: ARTIFICIAL SEQUENCE
<220> FEATURE:
<223> OTHER INFORMATION: CONTROL PEPTIDE

<400> SEQUENCE: 4

Arg Arg Arg Arg Ser Arg Arg Arg Arg Arg Phe Gly Arg Arg
1               5                   10                  15

Arg Arg Arg Val Trp Arg Arg Arg Lys Pro Lys Arg Lys Val Lys
                20                  25                  30

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: ANTISENSE OLIGONUCLEOTIDE

<400> SEQUENCE: 5
gttctcgctg gtgagtttca                                           20

<210> SEQ ID NO 6
<211> LENGTH: 18
<212> TYPE: DNA
<213> ORGANISM: ARTIFICIAL SEQUENCE
<220> FEATURE:
<223> OTHER INFORMATION: ANTISENSE OLIGONUCLEOTIDE

<400> SEQUENCE: 6
tctcccagcg tgcgccat                                             18
```

```
<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SCRAMBLED ANTISENSE OLIGONUCLEOTIDE

<400> SEQUENCE: 7
ggttttacca tcggttctgg                                              20

<210> SEQ ID NO 8
<211> LENGTH: 5
<212> TYPE: PRT
<213> ORGANISM: ARTIFICIAL SEQUENCE
<220> FEATURE:
<223> OTHER INFORMATION: ER-RETAINING PEPTIDE, SOURCE UNKNOWN

<400> SEQUENCE: 8

Tyr Lys Asp Glu Leu
1               5

<210> SEQ ID NO 9
<211> LENGTH: 7
<212> TYPE: PRT
<213> ORGANISM: Simian virus 40

<400> SEQUENCE: 9

Pro Lys Lys Lys Arg Lys Val
1               5
```

US 6,867,043 B2

PEPTIDES THAT DELIVER ANTISENSE OLIGONUCLEOTIDES WHICH DOWNREGULATE PROTEIN EXPRESSION IN CELLS

BACKGROUND OF THE INVENTION

Throughout this application, various publications are referenced in parentheses by arabic numbers. Full citations for these references may be found at the end of the specification immediately preceding the claims. The disclosures of these publications in their entireties are hereby incorporated by reference into this application to more fully describe the state of the art to which this invention pertains.

Cancer is the second leading cause of death in the United States. When cancer has metastasized, it can only be cured by systemic therapy, usually cytotoxic chemotherapy. However, it is often true that in this case chemotherapy is ineffective. There are currently attempts to develop new anti-cancer agents, including antisense oligonucleotides. Antisense oligonucleotides can specifically inhibit the translation of mRNA into protein. However, their use as therapeutic agents is limited because of intracellular transport and compartmentalization problems.

Thus, there are difficulties associated with delivery of antisense oligonucleotides to their targets. At least in tissue culture, antisense oligonucleotides almost invariably must be condensed with a delivery reagent to ensure adequate cellular uptake and release from sequestered sites in the endosomes/lysosomes. The most commonly employed delivery reagents are cationic lipids (e.g., Lipofectin), but these reagents may contribute their own cytotoxic effects, which affects the phenotype produced after treatment of the cells with the antisense effector molecule.

Accordingly, a large number of peptide delivery vehicles for antisense oligonucleotides have been devised. There are at least 20 peptides that increase the delivery of oligonucleotides to cells. These include pH sensitive fusogenic peptides, Antennapedia-type peptides, and the HIV tat C-terminus peptide. Other peptides that have been covalently conjugated to oligonucleotides include the ER-retaining peptide YKDEL (1) (SEQ ID NO:8), and various nuclear localization signal peptides (including the PKKKRKV sequence, SEQ ID NO:9, derived from the SV40 large-T antigen (2,3,4,5).

Non-covalent peptide oligonucleotide complexes have also been employed to increase cellular delivery (reviewed in 6). Morris, et al. (7) used a 27-mer peptide, called MPG, which was composed of the N-terminal domain of the HIV gp41 fusion sequence fused to the C-termain domain derived from the nuclear localization signal derived from the SV40 large-T antigen has. Nuclear localization of oligonucleotide in fibroblasts was observed. Pichon, et al. (11) employed a permeabilizing peptide derived ultimately from an analog of the N-terminal sequence of the HA2 subunit of the influenza virus hemeaglutinin. Permeabilization was successful as judged by the nuclear localization of a fluoresceinated oligonucleotide. Pichon et al. (12) subsequently employed histidylated oligolysines to deliver antisense oligonucleotides targeted to ICAM-1, and demonstrated excellent antisense activity. However, in almost all the examples of peptide-mediated delivery given above, it is unclear if any sequence specific downregulation of the expression of a target mRNA was observed. An effective non-lipidic way of reliably delivering functioning antisense oligonucleotides is still sought.

SUMMARY OF THE INVENTION

This invention provides a peptide comprising consecutive amino acids, the sequence of which amino acids is shown in SEQ ID NO: 2 and a composition comprising a complex between the peptide and an oligonucleotide, for example an oligonucleotide which comprises consecutive nucleotides having the sequence shown in SEQ ID NO:5 or SEQ ID NO:6, an oligonucleotide which comprises a sequence capable of inhibiting translation of a mRNA into a protein, an oligonucleotide which comprises phosphorothioate linkages, an oligonucleotide which comprises between 10 and 40 consecutive nucleotides and an oligonucleotide that comprises more than 40 consecutive nucleotides. This invention provides the instant peptide, wherein the peptide is membrane permeable.

This invention also provides a method of delivering an oligonucleotide into a cell comprising:
a) first contacting the cell with a lysosomotropic agent, and
b) then contacting the cell with the composition, under conditions permitting the composition to enter the cell and thereby deliver the oligonucleotide into the cell. The invention provides the instant method wherein the lysosomotropic agent is chloroquine.

This invention also provides a method of inhibiting expression of a protein in a cell comprising delivering an oligonucleotide into the cell using the instant method, under conditions permitting the oligonucleotide, once inside the cell, to hybridize with a nucleic acid encoding the protein and thereby inhibit expression of the protein from the nucleic acid in the cell, for example inhibiting expression of Protein Kinase C alpha in for example a mammalian cell, which may be of human origin and/or cancerous. The nucleic acid may be a deoxyribonucleic acid or a ribonucleic acid such as a messenger ribonucleic acid.

This invention provides a peptide comprising consecutive amino acids, the sequence of which amino acids is shown in SEQ ID NO: 1 and a composition comprising a complex between the peptide and an oligonucleotide, for example an oligonucleotide which comprises consecutive nucleotides having the sequence shown in SEQ ID NO:5 or SEQ ID NO:6, an oligonucleotide which comprises a sequence capable of inhibiting translation of a mRNA into a protein, an oligonucleotide which comprises phosphorothioate linkages, an oligonucleotide which comprises between 10 and 40 consecutive nucleotides and an oligonucleotide that comprises more than 40 consecutive nucleotides. This invention provides the instant peptide, wherein the peptide is membrane permeable.

This invention provides a method of delivering an oligonucleotide into a cell comprising contacting the cell with the instant composition, under conditions permitting the composition to enter the cell and thereby deliver the oligonucleotide into the cell.

This invention provides a method of inhibiting expression of a protein in a cell comprising delivering an oligonucleotide into the cell using the method, under conditions permitting the oligonucleotide, once inside the cell, to hybridize with a nucleic acid encoding the protein and thereby inhibit expression of the protein from the nucleic acid in the cell, for example inhibiting expression of Protein Kinase C alpha in for example a mammalian cell, which may be of human origin and/or cancerous. The nucleic acid may be a deoxyribonucleic acid or a ribonucleic acid such as a messenger ribonucleic acid.

This invention provides a method of increasing the sensitivity of a cancer cell to an anti-cancer agent e.g. paclitaxel comprising inhibiting expression of a protein in the cancer cell, for example inhibiting expression of protein kinase C alpha in for example a bladder cancer cell, using the instant method.

This invention provides a pharmaceutical composition comprising a therapeutically effective amount of either of the instant compositions and a pharmaceutically acceptable carrier.

This invention provides a method of making either of the instant compositions, comprising contacting an oligonucleotide with either of the instant peptides under conditions permitting the peptide to complex with the oligonucleotide.

This invention provides either of the instant compositions, wherein the oligonucleotide is between 10 and 40 consecutive nucleotides.

This invention also provides either of the instant compositions, wherein the oligonucleotide is longer than 40 consecutive nucleotides.

This invention provides a method of delivering an oligonucleotide into a cell comprising contacting the cell with either of the instant compositions, under conditions permitting the composition to enter the cell and thereby deliver the oligonucleotide into the cell.

BRIEF DESCRIPTION OF THE FIGURES

FIG. 5: This figure is a Western Blot showing inhibition of PKC-α protein expression in PC3 cells by ISIS 3521 (0.25, 1, 1.5, 2 μM) (SEQ ID NO:5) complexed in a fixed ratio with 1-protamine-NLS (SEQ ID NO:1). Note that chloroquine is necessary for efficacy. The peptide itself has no effect (not shown).

FIGS. 7a–b: (a) This Western blot of PC3 cells treated with 1-protamine-NLS (SEQ ID NO:1) complexed with ISIS 3521 (SEQ ID NO:5) shows that reliable inhibition of PKC-α protein expression can occur with 250 nM oligonucleotide concentration in the presence of 25 μM chloroquine. (b) This Western blot of PC3 cells treated with 1-protamine-NLS (SEQ ID NO:1) complexed with G3139 (SEQ ID NO:6) shows that the long peptide also delivers functional G3139 antisense to cells resulting in inhibition of bcl-2 protein expression in the presence of 25 μM chloroquine.

DETAILED DESCRIPTION OF THE INVENTION

Figure 1:
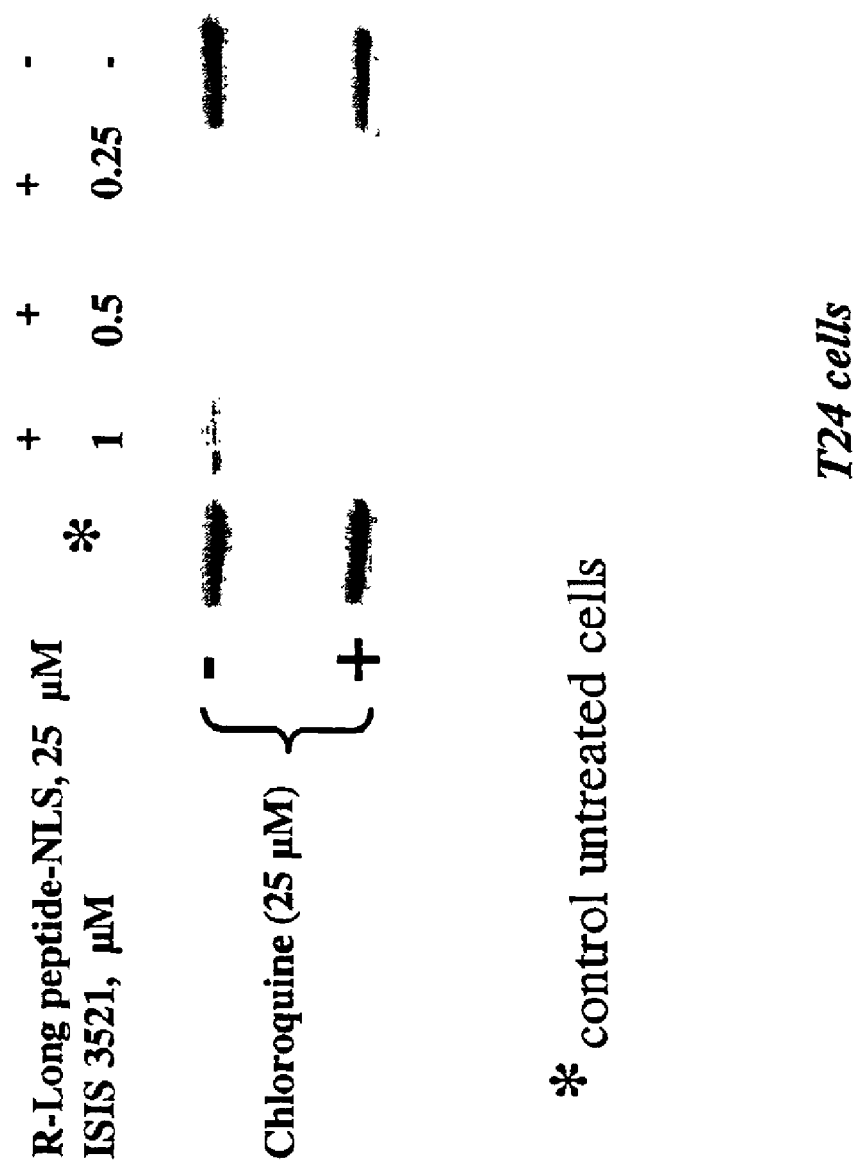
FIG. 1: Western Blot showing inhibition of PKC-α protein expression in T24 cells by ISIS 3521 (0.25, 0.5 and 1 μM) (SEQ ID NO:5) complexed with 1-protamine-NLS (SEQ ID NO:1). Note that chloroquine is not necessary for efficacy. The peptide itself has no effect (not shown).

The following definitions are presented as an aid in understanding this invention:

| | |
|---|---|
| A | Adenine; |
| C | Cytosine; |
| DNA | Deoxyribonucleic acid; |
| EGTA | Ethylene glycol-bis(beta-aminoethyl ether) -N,N,N',N'-tetraacetic acid; |
| ER | Endoplasmic reticulum; |
| FBS | Fetal bovine serum; |
| G | Guanine; |
| HIV | Human immunodeficiency virus; |
| HPLC | High pressure liquid chromatography; |
| ICAM | Intercellular cell adhesion molecule; |
| l-protamine | long protamine peptide; |
| MEM | Modified Eagle's medium; |
| mRNA | Messenger ribonucleic acid; |
| NLS | Nuclear localization signal; |
| PBS | Phosphate buffered saline; |
| PKC-α | Protein kinase C alpha; |
| RPMI media | Rockwell Park Memorial Institute media; |
| s-protamine | Short protamine peptide; |
| SV40 | Simian virus 40; |
| T | Thymine; |
| TBS | Tris buffered saline; and |
| Trp | Tryptophane. |

"Antisense oligonucleotide", as used herein, refers to oligonucleotides which are complementary to a specific DNA or RNA sequence which, once introduced into a cell, the combine with natural sequences produced by the cell to form duplexes. These duplexes can then block either further transcription or translation.

"Complex", as used herein refers to an association of a peptide with an oligonucleotide.

"Phosphorothioate", when applied to an oligonucleotide, shall mean an oligonucleotide in which a sulfur atom replaces one or more of the non-bridging oxygen atoms in one or more phosphodiester linkages, i.e. an oligonucleotide having one or more phosphorothiodiester linkages.

This invention provides a peptide comprising consecutive amino acids, the sequence of which amino acids is shown in SEQ ID NO: 2. For example, the peptide per se, a peptide with 1–20 amino acids at either or both ends, a peptide with more than 20 amino acids at either or both ends. Preferably the peptide is membrane permeable.

This invention also provides a composition comprising a complex between the peptide and an oligonucleotide. Desirably the oligonucleotide comprises from about 10 to about 40 consecutive nucleotides and has a sequence capable of inhibiting translation of a mRNA into a protein. Preferably the oligonucleotide comprises one or more phosphorothioate linkages. In one embodiment the oligonucleotide has more than 40 consecutive nucleotides. This invention also provides the instant composition further comprising an aqueous carrier, e.g. salines including phosphate buffered saline.

This invention further provides a method of delivering an oligonucleotide into a cell comprising:
a) first contacting the cell with a lysosomotropic agent, and
b) then contacting the cell with the composition, under conditions permitting the composition to enter the cell and thereby deliver the oligonucleotide into the cell. In one embodiment the lysosomotropic agent is chloroquine. In alternative embodiments the lysosomotropic agent is any lysosomotropic amine such as dendrimers, poly-l-lysine, porphyrins. In one embodiment the oligonucleotide comprises consecutive nucleotides having the sequence shown in SEQ ID NO:5. In another embodiment the oligonucleotide comprises consecutive nucleotides having the sequence shown in SEQ ID NO:6. Desirably the oligonucleotide is an antisense oligonucleotide.

This invention still further provides a method of inhibiting expression of a protein in a cell comprising delivering an oligonucleotide into the cell, under conditions permitting the oligonucleotide, once inside the cell, to hybridize with a nucleic acid encoding the protein and thereby inhibit expression of the protein from the nucleic acid in the cell. In one embodiment the protein is Protein Kinase C alpha. Desirably the cell is of mammalian origin, preferably of human origin. In one embodiment the cell is a cancer cell e.g. a bladder cancer cell, or any human cancer cell. The nucleic acid may be a deoxyribonucleic acid, or a ribonucleic acid, particularly a messenger ribonucleic acid.

In addition this invention provides a peptide comprising consecutive amino acids, the sequence of which amino acids is shown in SEQ ID NO: 1. Preferably the peptide is membrane permeable.

This invention also provides a composition comprising a complex between the peptide and an oligonucleotide. Desirably the oligonucleotide comprises from about 10 to about 40 consecutive nucleotides and has a sequence capable of inhibiting translation of a mRNA into a protein. Preferably the oligonucleotide comprises one or more phosphorothioate linkages. In one embodiment the oligonucleotide has more than 40 consecutive nucleotides. This invention also provides the instant composition further comprising an aqueous carrier, e.g. salines including phosphate buffered saline.

This invention further provides a method of delivering an oligonucleotide into a cell comprising contacting the cell with the second composition, under conditions permitting the composition to enter the cell and thereby deliver the oligonucleotide present in the composition into the cell. In one embodiment the oligonucleotide comprises consecutive nucleotides having the sequence shown in SEQ ID NO:5. In another embodiment the oligonucleotide comprises consecutive nucleotides having the sequence shown in SEQ ID NO:6. In one embodiment the conditions comprise contacting the cell with a lysosomotropic agent prior to contacting the cell with the composition. In one embodiment the lysosomotropic agent is chloroquine. In alternative embodiments the lysosomotropic agent is any lysosomotropic amine such as dendrimers, poly-l-lysine, porphyrins.

This invention still further provides a method of inhibiting expression of a protein in a cell comprising delivering an oligonucleotide into the cell, under conditions permitting the oligonucleotide, once inside the cell, to hybridize with a nucleic acid encoding the protein and thereby inhibit expression of the protein from the nucleic acid in the cell. In one embodiment the protein is Protein Kinase C alpha. Desirably the cell is of mammalian origin preferably of human origin. In one embodiment the cell is a cancer cell e.g. a bladder cancer cell or any human cancer cell. The nucleic acid may be a deoxyribonucleic acid or a ribonucleic acid, preferably a messenger ribonucleic acid.

This invention also provides a method of increasing the sensitivity of a cancer cell to an anti-cancer agent by inhibiting expression of a protein in the cancer cell using the instant method. In one embodiment the anti-cancer agent is paclitaxel. In one embodiment the cancer cell is a bladder cancer cell. In one embodiment the protein is kinase C alpha. In other embodiments the cancer cell is any human cancer cell.

This invention also provides a pharmaceutical composition comprising a therapeutically effective amount of either of the instant compositions and a pharmaceutically acceptable carrier. Various of such carriers known to those skilled in the art. For example, the carrier may be a membrane-permeable cationic reagent, a polyamidodendrimers; transferrin polylysine; polyglycolic acid co-polymers and any delivery in polymers that can be used to nanoencapsulate, such as polylactic acid, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone, transdermal enhancers, transmucosal delivery systems such as patches, tablets, suppositories, pessaries, gels and creams, which can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid). Injectable systems include solutions, suspensions, gels, microspheres and polymeric injectables, and can comprise excipients such as solubility-altering agents (e.g., ethanol, propylene glycol and sucrose) and polymers (e.g., polycaprolactones and PLGA's). Implantable systems include rods and discs, and can contain excipients such as PLGA and polycaprolactone.

Oral delivery systems include tablets and capsules. These can contain excipients such as binders (e.g., hydroxypropylmethylcellulose, polyvinyl pyrrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

This invention provides a method of making either of the instant compositions, comprising contacting an oligonucleotide with either of the instant peptides under conditions permitting the peptide to complex with the oligonucleotide.

This invention provides either of the instant compositions, wherein the oligonucleotide is longer than 40 consecutive nucleotides.

This invention provides a method of delivering an oligonucleotide into a cell comprising contacting the cell with either of the instant compositions, under conditions permitting the composition to enter the cell and thereby deliver the oligonucleotide into the cell. Such delivery may comprise gene delivery.

This invention will be better understood by reference to the Experimental Details which follow, but those skilled in the art will readily appreciate that the specific experiments detailed are only illustrative of the invention as described more fully in the claims which follow thereafter.

Experimental Details

The antisense oligonucleotide we have employed is the 20-mer phosphorothioate antisense PKC-α, first developed by Dean and colleagues (13), named ISIS 3521 (SEQ ID NO:5). This, and the 18-mer antisense bcl-2 oligonucleotide G3139 (SEQ ID NO:6) that we have also employed in this study, are widely considered to be sequence-specific inhibitors of gene expression. Because of this property, they are both well suited for the evaluation of a novel delivery strategy.

Peptide Synthesis

We have designed peptides in a attempt to satisfy the major requirements for efficient gene delivery and antisense activity. These requirements include: the ability to cross the cell membrane, the high affinity and specificity for oligonucleotides, and nuclear addressing. The peptides also should have a Trp residue which can act as an intrinsic probe for monitoring the interactions with oligonucleotides. The peptides were designed as bifunctional peptides.

This invention discloses peptides composed of a hydrophobic N-terminal DNA-binding domain which is a protamine fragment required for efficient crossing of the cell membrane, and a hydrophilic C-terminal nuclear localization signal (NLS) derived from the SV40 large T-antigen, required for the nuclear targeting.

There is a large family of nuclear localization signals, but we chose the simian virus SV40 large T-antigen nuclear localization sequence because it has been shown to enhance cellular uptake of DNA (8, 9). The peptide employed here consists of a basic stretch of amino acids containing five consecutive positively charged residues which are necessary for nuclear import. Successful transfection of DNA into cells in culture, by using mixtures of DNA and NLS protein, has resulted in efficient DNA transfer into the nucleus and enhanced transgene expression (8, 10).

The two peptides disclosed here differ in that one was designed to possess a long Arg-rich peptide with NLS; the other peptide has a shorter protamine fragment. These two peptides are respectively referred to as l-protamine-NLS (SEQ ID NO:1) and s-protamine-NLS (SEQ ID NO:2).

Peptides form Complexes with Oligodeoxynucleotides

The interaction of ISIS 3521 (SEQ ID NO:5), a 20mer phosphorothioate antisense oligonucleotide, with the short and long protamine-NLS peptides (s-protamine-NLS and l-protamine-NLS) was evaluated by fluorescence spectroscopy. The peptide contains a single Trp residue (position 8 of the short peptide; SEQ ID NO:2) which can be excited at 290 nm and emits fluorescent light at 330 nm. The ability of a bound oligonucleotide to quench this fluorescent emission constitutes a relatively sensitive probe for the monitoring of molecular interactions.

The titration of a 5 μM solution of s-protamine-NLS (SEQ ID NO:2) with increasing concentrations of ISIS 3521 (SEQ ID NO:5), both in PBS and in Opti-MEM (without serum, to mimic transfection conditions), led to dramatic fluorescence quenching. At least two oligonucleotide binding modes can be easily discerned: At low oligonucleotide concentration (relative to s-protamine-NLS peptide) a plot of the decrease in fluorescence (due to quenching) vs. oligonucleotide concentration fits an equation of the Michaelis-Menton type. A Lineweaver-Burke (double reciprocal) plot gives Kd=80 nM ($R^2$=0.99). However, as oligonucleotide concentration is increased, Trp fluorescence continues to decline, but a similar plot no longer fits a Michaelis-Menton-type equation, and the binding becomes increasingly complex. Trp fluorescence is finally completely quenched (i.e., 100%) at a 4:1 molar ratio of peptide/oligonucleotide.

Protamine-NLS Peptides Deliver Oligonucleotides to the Cell Nucleus

The ability of the protamine-NLS peptides to deliver the oligonucleotides into the cell nucleus was evaluated by fluorescence confocal microscopy. 5'-fluorescein-labeled ISIS 3521 (2 μM) (SEQ ID NO:5) was complexed with s-protamine-NLS (SEQ ID NO:2) at a peptide/oligonucleotide charge ratio 3.15:1 and 2.37:1 (2 μM oligonucleotide; 8 μM and 6 μM peptide concentrations, respectively) and incubated with T24 cells pretreated for 15 min with chloroquine (25 μM in Opti-MEM). The peptide effectively delivered fluoresceinated oligonucleotide to the cell nucleus after an incubation time of 24 hr. In the absence of peptide, oligonucleotides were internalized poorly by the cells, with most of the internalized material accumulating in a punctate pattern, signifying localization in vesicular structures (endosomes/lysosomes).

Under the same conditions and reagent concentrations, the control peptide, s-protamine-scrambled NLS (SEQ ID NO:3), also promotes the delivery of the oligonucleotide to the nucleus. Significantly, however, when delivered in this fashion, the oligonucleotide does not downregulate the expression of PKC-α protein as determined by Western blotting.

Peptide-oligodeoxynucleotide Complexes Demonstrate Antisense Activity

Short Peptide

Experiments using the protamine-NLS peptides to deliver antisense oligonucleotides were performed in T24 bladder carcinoma and PC-3 prostate carcinoma cells. In addition to the 20-mer ISIS 3521, the 18-mer phosphorothioate oligonucleotide G3139 (SEQ ID NO:6) was also employed. G3139 is targeted to the first six codons of the human bcl-2 open reading frame. The optimum incubation time of the cells with the peptide/oligonucleotide complexes was 24 hr. For experiments with s-protamine-NLS (SEQ ID NO:2) cells were pretreated with 25 μM of chloroquine for 15 min. The expression of PKC-α protein was assayed by Western blotting after 24 hr, while the expression of bcl-2 protein in PC3 cells was assayed similarly after a further 48 hr incubation in RPMI media containing 10% FBS. In both cases, the incubations were performed in the continuous presence of the peptide/oligonucleotide complexes.

Figure 4:
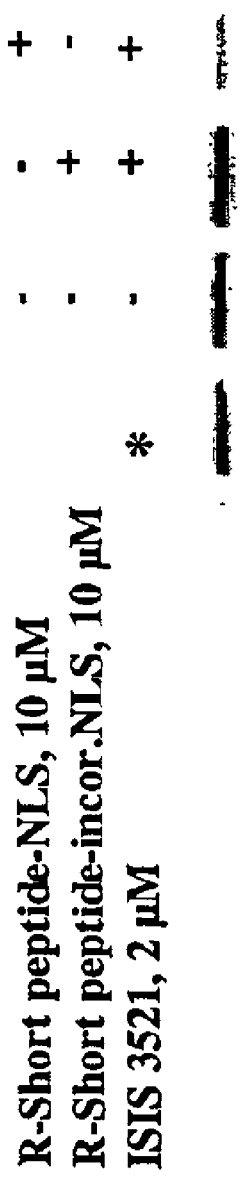
FIG. 4: This figure shows that the correct NLS sequence is required for efficacy of the s-protamine-NLS (SEQ ID NO:2)/oligonucleotide complex in T24 cells. When complexed with the scrambled NLS sequence (SEQ ID NO:3) no antisense activity by ISIS 3521 (SEQ ID NO:5) is detected.
Figure 9:
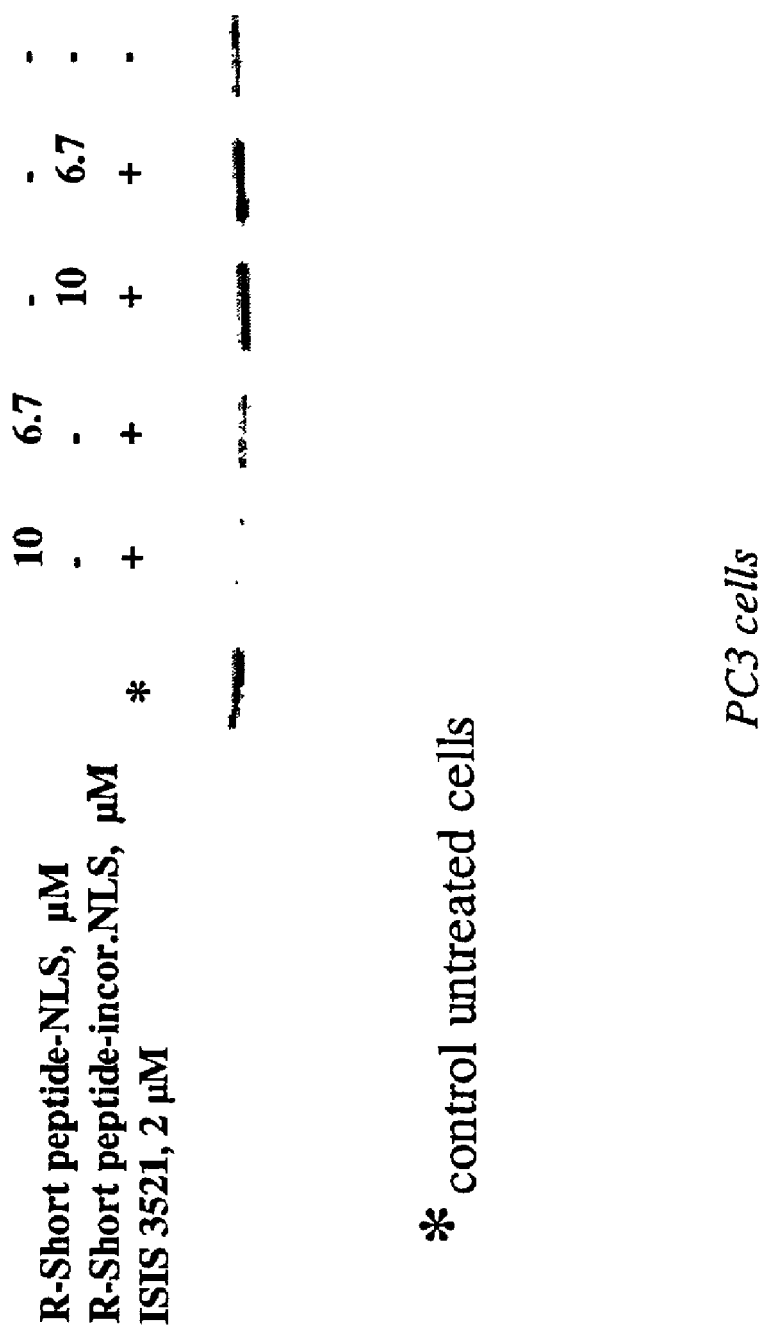
FIG. 9: The antisense efficacy of s-protamine-NLS (SEQ ID NO:2) is dependent on the integrity of NLS in PC3 cells as shown by the lack of inhibition of protein expression by s-protamine-(scrambled)NLS (SEQ ID NO:3) in this figure. At the same peptide concentrations of 10 μM and 6.7 μM the s-protamine-NLS (SEQ ID NO:2) delivery of ISIS 3521 (SEQ ID NO:5) results in a much greater inhibition of protein expression.

The s-protamine-NLS (SEQ ID NO:2), when complexed to ISIS 3521 (2 μM) (SEQ ID NO:5) at a 4:1 or 3:1 molar ratio (3.15 and 2.37 charge ratio, respectively) of peptide/oligonucleotide yielded significant antisense activity in both T24 (FIG. 4.) and PC-3 cells (FIG. 9). By Western blotting and scanning densitometry, the expression of the PKC-α (T24 and PC-3 cells) and Bcl-2 (PC3 cells) proteins was reduced by approximately 80%, 80% and 70%, respectively. Naked oligomer (i.e., not complexed with peptide) at the identical concentration (2 μM)+25 μM chloroquine preincubation was completely ineffective, most likely because of the sequestration of the oligonucleotides in endosomes/lysosomes, as demonstrated by confocal microscopy. A control, scrambled phosphorothioate oligonucleotide (ISIS 4559, SEQ ID NO:7) complexed with the s-protamine-NLS (SEQ ID NO:2) and a complex of ISIS 3521 (SEQ ID NO:5) with s-protamine-scrambled-NLS (SEQ ID NO:3) under identical conditions (+25 μM chloroquine preincubation) did not produce any reduction in target PKC-α protein levels in PC3 cells (FIG. 9). Furthermore, 25 μM chloroquine alone did not downregulate PKC-α expression in either cell line.

Figure 6:
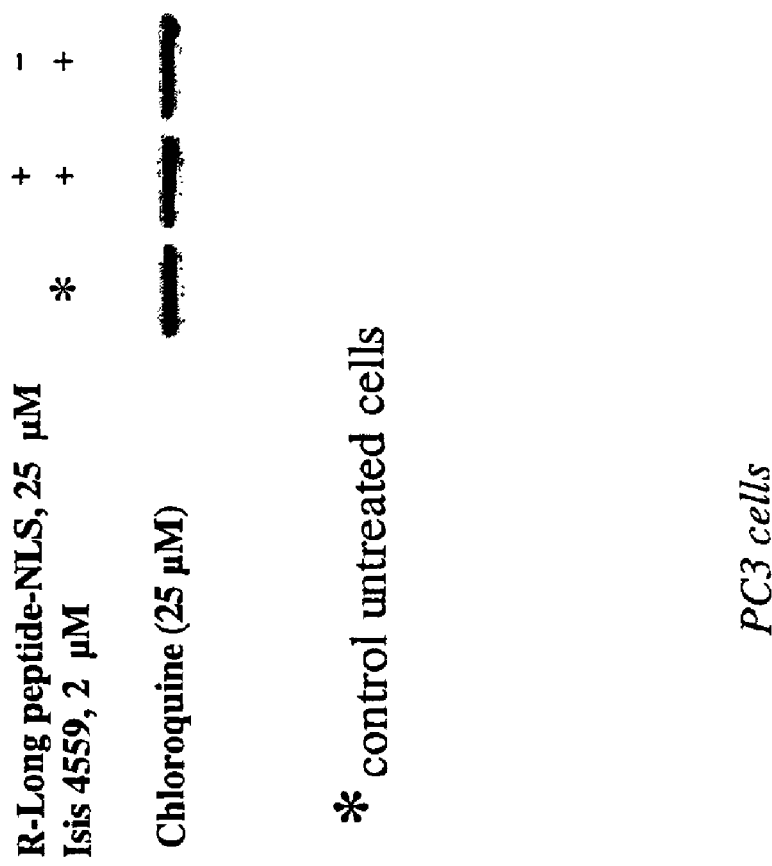
FIG. 6: This figure shows a lack of inhibition of PKC-α protein expression in PC3 cells by the control oligonucleotide ISIS 4559 (2 μM) (SEQ ID NO:7) complexed with 1-protamine-NLS (SEQ ID NO:1). Note that even in the presence of chloroquine no inhibition occurs.

In addition, G3139 (SEQ ID NO:6) when complexed to s-protamine-NLS (SEQ ID NO:2) was "antisense" active in PC-3 cells. Similar controls as employed above (scrambled oligonucleotide (see FIG. 6), scrambled NLS sequence, chloroquine alone) were all totally inactive. Approximately 70% inhibition of Bcl-2 expression could be obtained with 4:1 and 3:1 molar ratios of peptide/oligonucleotide.

Long Peptide

Figure 2:
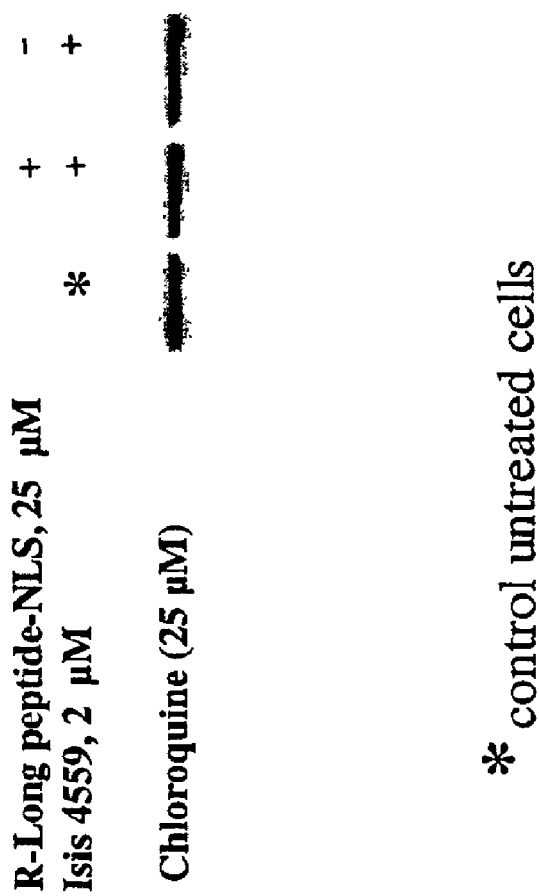
FIG. 2: This figure shows a lack of inhibition of PKC-α protein expression in T24 cells by the control oligonucleotide ISIS 4559 (2 μM) (SEQ ID NO:7) complexed with 1-protamine-NLS (SEQ ID NO:1). Note that even in the presence of chloroquine no inhibition occurs.
Figure 3:
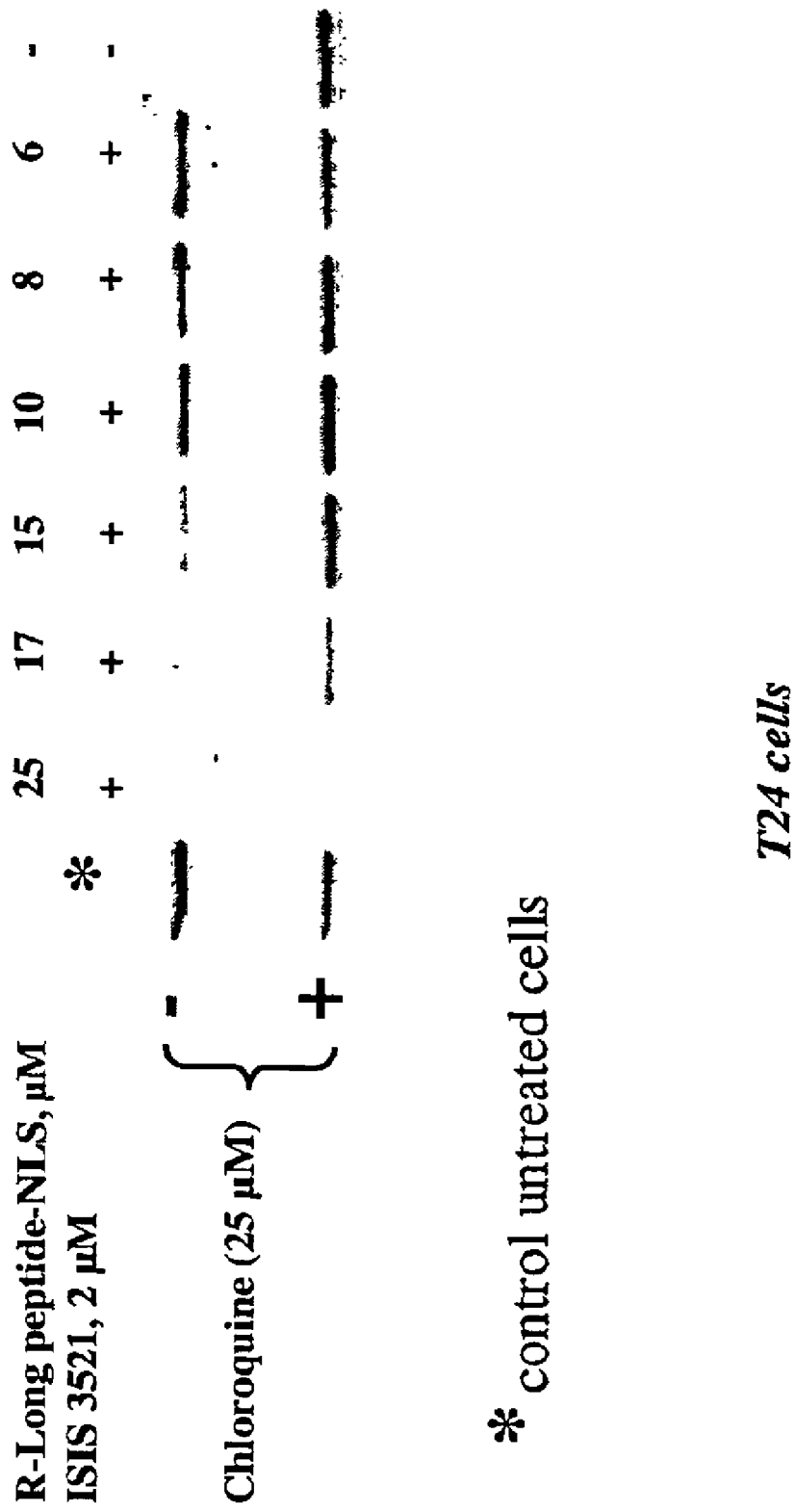
FIG. 3: This figure shows increasing peptide:oligonucleotide ratio diminishes antisense efficacy in T24 cells. The optimum peptide concentration is 25 μM.

The ability of 1-protamine-NLS (SEQ ID NO:1) to diminish PKC-α and Bcl-2 protein expression in T24 and PC-3 cells was also evaluated. Complexes of this peptide with ISIS 3521 (see FIG. 1) and G3139 oligonucleotides (see FIG. 7b) were active over approximately the same concentration range in both cell lines. In T24 cells, expression of PKC-α (FIG. 1) and Bcl-2 proteins were reduced. However it is notable that chloroquine pretreatment was not required for inhibition of protein expression in T24 cells when the l-protamine-NLS was used to deliver the oligonucleotide (FIG. 1). Controls of l-protamine-NLS complexed with ISIS 4559 did not inhibit protein expression (see FIG. 2). The ratio of peptide:oligonucleotide affected the antisense efficacy (see FIG. 3).

Figure 8:
FIG. 8: The antisense efficacy of 1-protamine-NLS is not so heavily dependent on the integrity of NLS in PC3 cells as it is in T24 cells as shown by slight inhibition of protein expression by 1-protamine-(scrambled)NLS (SEQ ID NO:4) in this figure. However, at the same peptide concentration of 25 μM the 1-protamine-NLS (SEQ ID NO:1) delivery of ISIS 3521 results in a much greater inhibition of protein expression.

In PC-3 cells protein expression was reduced by the peptide-oligonucleotide complex (see FIG. 5 and FIG. 7a), but the cells did require pre-treatment with 25 μM chloroquine for this effect to be observed. Controls, such as ISIS 3521 complexed with 1-protamine-scrambled NLS (SEQ ID NO:4) had a reduced effect (see FIG. 8) and ISIS 3521 (SEQ ID NO:5) alone did not have antisense effects.

It is clear that other agents similar to chloroquine could be used in place of chloroquine to effect the same purpose. Also oligonucleotides longer than 40 nucleotides could be complexed with peptides for cell delivery.

Downregulation of PKC-α Increases Sensitivity of T24 Bladder Carcinoma Cells to Paclitaxel As a measure of the effectiveness of the peptide-delivered antisense inhibition of PKC-α the cells treated with peptide were exposed to paclitaxel, a compound commonly used in cancer therapy to inhibit microtubule depolymerization.

After 3 days of paclitaxel treatment T24 cells were treated for 24 hours with s-protamine-NLS (8 μM)/ISIS 3521 (2 μM) complexes (3.15:1 charge ratio) after pretreatment with 25 μM chloroquine. ISIS 3521, s-protamine-NLS peptide (SEQ ID NO:2) and 25 μM chloroquine alone had no effect on cell viability. Complexes of s-protamine-scrambled-NLS/ISIS 3521 and s-protamine-NLS/scrambled ISIS 3521 also did not reduce cellular viability. Only treatment of the cells with s-protamine-NLS/ISIS 3521 was able to reduce cellular viability as measured by the reduction in cell proliferation determined by 3-(4,5-dimethylthiazol-2-yl)-2, 5-diphenyl tetrazolium bromide (MTT) assay.

Materials and Methods

Peptide Synthesis: Peptide synthesis was carried out on a Rainin PS3 Automated Solid Phase Peptide Synthesiser using standard FMOC chemistry. Standard deprotection and cleavage methods were employed, by treating the peptide with a mixture containing 95% TFA, 2.5% triisopropylsilane and 2.5% $H_2O$ (4 ml), for 2 hours at room temperature with constant stirring. The peptide was then isolated by ether extraction.

Purification and Characterization of the Peptides: Reverse phase HPLC was carried out using a Vydac 218TP C18 protein and peptide RP 5M column (4.6×250 mm) on a Waters 996 Photodiode Array Detector. Samples were monitored at 254 nm and a mobile gradient buffer system used. Mobile phase A was 0.1M trimethylammonium bicarbonate (pH 7.0) and mobile phase B was HPLC grade acetonitrile.

Matrix assisted laser desorption ionization-time of flight mass spectrometry (MALDI-TOF) was carried out on a Bruker Biflex spectrometer and all data was collected and analysed using Solaris software. Peptides were analyzed in positive linear mode as 50 pM in 3:7 acetonitrile/water and 0.1% trifluoroacetic acid. Molecular weight of peptide SEQ ID NO:2 is 2998.97 ($M/Z^{+1}$ 3000). Molecular weight of peptide SEQ ID NO:1 is 4580.0 ($M/Z^+$4580.9).

Cell culture: T24 cells were grown in McCoy's 5A medium (Gibco BRL, Grand Island, N.Y.), containing 10% (v/v) heat inactivated (56° C.) fetal bovine serum (FBS) (Gibco BRL, Grand Island, N.Y.), supplemented with 25 mM Hepes, 100 units/mL penicillin G sodium and 100 g/mL streptomycin sulfate. PC-3 cells were grown in RPMI 1640 medium (Gibco BRL), containing 10% (v/v) FBS, to which was added 2 mM glutamine, 1 mM sodium pyruvate, 0.1 mM non essential amino acids. Stock cultures were maintained at 37° C. in a humidified 5% $Co_2$ incubator.

Reagents: The anti-PKC-alpha mouse monoclonal antibody was purchased from Transduction Laboratories (Lexington, Ky.). The anti-bcl-2 mouse monoclonal antibody was purchased from Dako (Carpinteria, Calif.). The anti-mouse horseradish peroxidase conjugated secondary antibody was from Amersham (Arlington Heights, Ill.).

Synthesis of oligonucleotides: Phosphorothioate oligonucleotides were synthesized on an Applied Biosystems (Foster City, Calif.) model 380B DNA. Following cleavage from controlled pore glass support, oligodeoxynucleotides were base deblocked in ammonium hydroxide at 60C for 8 hours and purified by reversed phase HPLC [0.1% TFA, TEAB/acetonitrile. PRP-1 support]. Oligomers were detritylated in 3% acetic acid and precipitated with 2% lithium perchlorate/acetone, dissolved in sterile water and reprecipitated as the sodium salt from 1 M NaCl/ethanol. Concentrations were determined by UV spectroscopy.

The sequences of the oligonucleotides used were: ISIS 3521 (targeted to the 3' region of the PKC-α mRNA), 5'-GTTCTCGCTGGTGAGTTTCA-3' (SEQ ID NO:5); G3139 (targeted to the first 6 codons of the human bcl-2 open reading frame), 5'-TCTCCCAGCGTGCGCCAT-3' (SEQ ID NO:6). The sequence of the control scrambled oligonucleotide (ISIS 4559) was 5'-GGTTTTACCAT-CGGTTCTGG-3' (SEQ ID NO:7).

Nature of the complex: The nature of the complex is not yet fully elucidated, it is thought that hydrogen of the positively charged guanidinium functional groups within it result in electrostatic interactions with the negatively charged phosphate backbone of the nucleic acid molecule.

Treatment of cells with oligonucleotide-peptide complexes: Cells were grown in six-well plates until 65-75% confluent. The peptides, at the stated peptide/ oligonucleotide molar ratios, were diluted in 500 μL of Opti-MEM medium and oligonucleotide was then added up to the required concentration of 2 μM. The solution was mixed gently and incubated at room temperature for 30 min to allow oligonucleotide-peptide complexes to form. Then the complexes were overlaid onto the cells, which had been rinsed with Opti-MEM medium and pretreated with 500 μL chloroquine (final concentration, 25 μM in Opti-MEM) for 15 min. The cells were then incubated at 37° C. for 24 hr (for PKC-α) or re-fed with complete McCoy's 5A media containing 10% FBS and allowed to incubate for an additional 72 hr (for bcl-2) before cell lysis and extract preparation.

Fluorescence titrations: Fluorescence experiments were performed on a luminescence spectrometer, Aminco Bowman series 2, SLM Aminco (Urbana, Ill.). The intrinsic tryptophan fluorescence of peptide was excited at 290 nm, and the emission spectrum was recorded between 310 and 410 nm with a spectral bandpass of 4 nm. A fixed concentration of protein (5 µM) was titrated by increasing the concentration of oligonucleotide (in a range of 0–1 µM) at room temperature in PBS buffer. Curve fitting was performed with the Grafit program (Excel Software).

Confocal microscopy: Cells were seeded in glass bottom microwells (MatTec Corp., Mass.), and treated with peptide-oligodeoxynucleotide complexes at 37° C. for 24 hr. Cellular internalization was examined using an LSM 410 laser scanning confocal microscope (Zeiss, Thornwood, N.Y.) equipped with a krypton/argon laser and attached to a Zeiss Axiovert 100 TV microscope. The 515–540 nm bandpass for fluorescein was used. Z-series were taken of a 1 to 2 micron optical section at 2 µm intervals. For measurements, a maximum projection of all sections was employed.

Western Blotting: Cells were treated with peptide-oligodeoxynucleotide complexes, scraped, washed with cold PBS and then extracted in 40–50 mL of lysis buffer [50 mM Tris-HCl, pH 7.5; 1% NP-40; 0.25% sodium deoxycholate; 150 mM NaCl; 1 mM EGTA; 50 µg/mL Pefablock™ SC; 15 µg/mL aprotinin, leupeptin, chymostatin, and pepstatin A; 1 mM $Na_3VO_4$; 1 mM NaF] at 4° C. for 1 hr. Cell debris was removed by centrifugation at 14,000×g for 20 min at 4° C. Protein concentrations were determined using the Bio-Rad protein assay system (Bio-Rad Laboratories, Richmond, Calif.).

Aliquots of cell extracts containing 20–30 µg of protein were resolved by 10% or 12% SDS-polyacrylamide gel electrophoresis and transferred to Hybond ECL filter paper (Amersham, Arlington Heights, Ill.). Filters were incubated at room temperature for 1–2 h in Blotto A [5% non-fat milk powder in TBS-T:10 mM Tris-HCl, pH 8.0, 150 mM NaCl, 0.05% Tween 20 (for PKC-α) and 5% BSA in PBS, 0.5% Tween (for Bcl-2)] and then probed overnight at 4° C. with 1:1000 dilution of anti-PKC- or 1:500 dilution of anti-Bcl-2 in Blotto A. After washing in TBS-T or PBS-T buffer (3×7 min, room temperature), filters were incubated for 1 h at room temperature in 5% milk/TBS-T or 5% milk/PBS-T buffer containing a 1:3,000 dilution of peroxidase-conjugated anti-mouse secondary antibody. The filters were then washed (3×10 min, room temperature), and ECL was performed according to the manufacturer's instructions (Amersham).

Cellular viability assay: Cells were seeded in 96-well tissue culture plates and treated the next day with oligonucleotide-peptide complexes for 24 hr. After 3 days treatment with paclitaxel (at the indicated concentrations as described in the Results), cellular viability was determined by 3-(4,5-dimethylthiazol-2-yl)-2,5-diphenyltetrazolium bromide (MTT) assay. The cells were incubated for 4 hr at 37° C., 5% CO2 with 0.5 mg/mL MTT in complete media. An equal volume of solubilization solution (10% SDS in 0.01 M HCl) was then added and allowed to incubate overnight at 37° C. After the formazan crystals were dissolved, the plates were read on a Dynatech MR600 Microplate Reader at 540 nm.

Statistical analysis of the results was performed using the Analysis ToolPack provided by Microsoft Excel. A Student's two-sample t-test, assuming unequal variances, was used to determine the equality of the means of two samples. The confidence level was 0.05.

References

1. Arar, K., Monsigny, M., and Mayer, R. (1993) Tetrahedron Lett. 34;3087–90
2. de la Torre, B., Albericio, F., Saison-Behmoaras, E., Bachi, A., and Eritja, R. (1999) Bioconjugate Chem., 10:1005-1–12
3. Eritja, r., Pons, A., Escarceller, M., Giralt, E., and Albericio, R. (1991) Tetrahedron 47:4113–4120
4. Reed, M., Fraga, D., Schwartz, D., choller, J., and Hinrichsen, R. (1995) Bioconjugate Chem. 6, 101–108
5. Neves, C., Byk, G., Scherman, D., and Wils, P. (1999) FEBS Lett. 453:41–45
6. Lebedeva, I., and Stein, C. A. "Antisense in Cancer: Recent Advances", BioDrugs, 2000, (13), 195–216.
7. Morris, M. C., Vidal, P. Chaloin, L., Heitz, F., and Divita, G. (1997) Nucl. Acids Res. 25:2730–2736
8. Collas P, Husebye H, Alestrom P. (1996) The nuclear localization sequence of the SV40 T antigen promotes transgene uptake and expression in zebrafish embryo nuclei. Transgenic Res. 5(6):451–8.
9. Collas P. and Alestrom P. (1997) Rapid targeting of plasmid DNA to zebrafish embryo nuclei by the nuclear localization signal of SV40 T antigen. Mol Mar Biol Biotechnol. 6(1):48–58.
10. Wienhues U, Hosokawa K, Hoveler A, Siegmann B, Doerfler W. (1987), A novel method for transfection and expression of reconstituted DNA-protein complexes in eukaryotic cells. DNA. 6(1):81–9.
11. Pichon C, Arar K, Stewart A J, Dodon M D., Gazzolo L, Courtoy P J, Mayer R, Monsigny M, Roche A C. (1997) Intracellular routing and inhibitory activity of oligonucleopeptides containing a KDEL motif. Mol Pharmacol. 51(3):431–8.
12. Pichon C, Roufai M B, Monsigny M, Midoux P. (2000) Histidylated oligolysines increase the transmembrane passage and the biological activity of antisense oligonucleotides. Nucleic Acids Res. 28(2):504–12
13. Dean N, McKay R, Miraglia L, Howard R, Cooper S, Giddings J, Nicklin P, Meister L, Ziel R, Geiger T, Muller M, Fabbro D. (1996) Inhibition of growth of human tumor cell lines in nude mice by an antisense of oligonucleotide inhibitor of protein kinase C-alpha expression. Cancer Res. 56(15):3499–507

What is claimed is:

1. A peptide comprising consecutive amino acids, the sequence of which amino acids is shown in SEQ ID NO:2.

2. The peptide of claim 1, wherein the peptide is membrane permeable.

3. A composition comprising a complex between the peptide of claim 1 and an oligonucleotide.

4. The composition of claim 3, further comprising an aqueous carrier.

5. The composition of claim 3, wherein the oligonucleotide comprises from about 10 to about 40 consecutive nucleotides.

6. The composition of claim 5, wherein the consecutive nucleotides of the oligonucleotide have a sequence capable of inhibiting translation of a mRNA into a protein.

7. The composition of claim 5, wherein the oligonucleotide comprises phosphorothioate linkages.

8. A method of delivering an oligonucleotide into a cell comprising:
  1) first contacting the cell with a lysosomotropic agent, and
  2) then contacting the cell with the composition of claim 3, under conditions permitting the composition to enter the cell and thereby deliver the oligonucleotide into the cell.

9. The method of claim 8, wherein the lysosomotorpic agent is chloroquine.

10. A method of inhibiting expression of a protein in a cell in vitro comprising delivering an oligonucleotide into the cell using the method of claim 8, under conditions permitting the oligonucleotide, once inside the cell, to hybridize with a nucleic acid encoding the protein and thereby inhibit expression of the protein from the nucleic acid in the cell.

11. The composition of claim 6, wherein the sequence of the oligonucleotide is shown in SEQ ID NO:5.

12. The method of claim 10, wherein the protein is Protein Kinase C alpha.

13. The method of claim 10, wherein the cell is of mammalian origin.

14. The method of claim 13, wherein the cell is of human origin.

15. The method of claim 14, wherein the cell is a cancer cell.

16. The method of claim 10, wherein the nucleic acid is a deoxyribonucleic acid.

17. The method of claim 10, wherein the nucleic acid is a ribonucleic acid.

18. The method of claim 17, wherein the ribonucleic acid is a messenger ribonucleic acid.

19. A method of making a composition, comprising contacting an oligonucleotide with the peptide of claim 1 under conditions permitting the peptide to form a complex with the oligonucleotide.

20. A method of increasing the sensitivity of a cancer cell to an anti-cancer agent which comprises inhibiting expression of a protein in the cancer cell in vitro using the method of claim 10.

21. The method of claim 20, wherein the anti-cancer agent is paclitaxel.

22. The method of claim 21, wherein the protein is protein kinase C alpha.

23. The method of claim 22, wherein the cancer cell is a bladder cancer cell.

24. The composition of claim 3, wherein the oligonucleotide is longer than 40 consecutive nucleotides.

25. A method of delivering an oligonucleotide into a cell comprising contacting the cell with the composition of claim 24, under conditions permitting the composition to enter the cell and thereby deliver the oligonucleotide into the cell.

26. A method of delivering an oligonucleotide comprising consecutive nucleotides, the sequence of which is set forth in SEQ ID NO:5, into a cell comprising:

(a) contacting the oligonucleotide with a peptide comprising consecutive amino acids the sequence of which is set forth in SEQ ID NO:2 under conditions permitting the oligonucleotide to form a complex with the peptide; and (b) contacting the cell with the complex of step (a), under conditions permitting the complex to enter the cell and thereby deliver the oligonucleotide into the cell.

* * * * *